(12) United States Patent
Alisi et al.

(10) Patent No.: US 8,455,519 B2
(45) Date of Patent: Jun. 4, 2013

(54) DRUG ACTIVE IN NEUROPATHIC PAIN

(75) Inventors: Maria Alessandra Alisi, Rome (IT); Nicola Cazzolla, Albano Laziale (IT); Guido Furlotti, Rome (IT); Angelo Guglielmotti, Rome (IT); Lorenzo Polenzani, Grottaferrata (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 337 days.

(21) Appl. No.: 12/738,499

(22) PCT Filed: Nov. 6, 2008

(86) PCT No.: PCT/EP2008/065081
§ 371 (c)(1),
(2), (4) Date: May 5, 2010

(87) PCT Pub. No.: WO2009/062883
PCT Pub. Date: May 22, 2009

(65) Prior Publication Data
US 2010/0215742 A1    Aug. 26, 2010

(30) Foreign Application Priority Data
Nov. 12, 2007 (EP) .................... 07425709

(51) Int. Cl.
C07D 211/32 (2006.01)
A61K 31/445 (2006.01)
(52) U.S. Cl.
USPC .......................... 514/318; 546/199
(58) Field of Classification Search
None
See application file for complete search history.

(56) References Cited

U.S. PATENT DOCUMENTS

| | | | |
|---|---|---|---|
| 6,197,769 B1 | 3/2001 | Alisi et al. | |
| 2002/0049229 A1 | 4/2002 | Yamamoto et al. | |
| 2006/0183775 A1 | 8/2006 | Guglielmotti et al. | |
| 2007/0010555 A1 | 1/2007 | Alisi et al. | |

FOREIGN PATENT DOCUMENTS

| | | |
|---|---|---|
| EP | 1 182 193 | 2/2002 |
| WO | 98 46589 | 10/1998 |
| WO | 2004 101548 | 11/2004 |
| WO | 2005 013989 | 2/2005 |

OTHER PUBLICATIONS

Wermuth, C. G., "13 Molecular Variations Based on Isosteric Replacements", The Practice of Medicinal Chemistry, pp. 203-237 (1996) XP 002190259 ISBN 0-12-744640-0.
Ashburn, M. A. et al., "Management of Chronic Pain", The Lancet, vol. 353, pp. 1865-1869 (May 29, 1999).
Woolf, C. J. et al., "Neuropathic Pain: Aetiology, Symptoms, Mechanisms, and Management", The Lancet, vol. 353, pp. 1959-1964 (Jun. 5, 1999).
Scholz, J. et al., "Can We Conquer Pain?", Review, Nature Neuroscience Supplement, vol. 5, pp. 1062-1067 (Nov. 2002).
Foreman, L. E. et al., "The Reaction of Organic Halides With Piperidine", V. Negatively Substituted Ethyl Bromides, Journal of the American Chemical Society, IBID, vol. 62, pp. 1435-1438 (Jun. 1940).
Martin, G. R. et al., "Classification Review Receptors for 5-Hydroxytryptamine: Current Perspectives on Classification and Nomenclature", Neuropharmacology, vol. 33, No. 3/4, pp. 261-273 (1994).
Hoyer, D. et .al., "Characterization of the 5-$HT_{1B}$ Recognition Site in Rat Brain: Binding Studies With (-)$I^{125}$ I Iodocyanpindolol", European Journal of Pharmacology, vol. 118, pp. 1-12 (1985).
Bonhaus, D. W. et al., "The Pharmacology and Distribution of Human 5-Hydroxytryptamine$_{2B}$(5-HT $_{2B}$) Receptor Gene Products: Comparison With 5-$HT_{2A}$ And 5-HT $_{2C}$Receptors", British Journal of Pharmacology, vol. 115, pp. 622-628 (1995).
Wolf, W. A., et al., "The Serotonin 5-HT $_{2C}$, Receptor Is a Prominent Serotonin Receptor in Basal Ganglia: Evidence From Functional Studies on Serotonin-Mediated Phosphoinositide Hydrolysis", Journal of Neurochemistry, vol. 69, No. 4, pp. 1449-1458 (1997).
Boess, F. G., et al., "Analysis of the Ligand Binding Site of Tehe 5-HT $_3$Receptor Using Site Directed Mutagenesis: Importance of Glutamate 106", Neuropharmacology, vol. 36, No. 4/5, pp. 637-647 (1997).
Mialet, J. et al., "Isolation of the Serotoninergic 5-$HT_{4(e)}$Receptor From Human Heart and Comparative Analysis of Its Pharmacological Profile in C6-Glial And CHO Cell Lines", British Journal of Pharmacology, vol. 129, pp. 771-781 (2000).

(Continued)

Primary Examiner — D M Seaman
Assistant Examiner — Heidi Reese
(74) Attorney, Agent, or Firm — Oblon, Spivak, McClelland, Maier & Neustadt, L.L.P.

(57) ABSTRACT

The present invention relates to a compound of formula (I): in which: R is a linear or branched alkyl group containing between 1 and 3 carbon atoms, Y is CH or N, and p is an integer between 0 and 3 and preferably 0 and 1, and salts thereof, either acid-addition salts with a pharmaceutically acceptable organic or mineral acid, or base-addition salts with a pharmaceutically acceptable organic or mineral base. The invention also relates to a process for preparing the compound of formula (I), and to a pharmaceutical composition comprising it. The invention also relates to the use of an indazole for preparing a pharmaceutical composition that is active in the treatment of neuropathic pain.

(I)

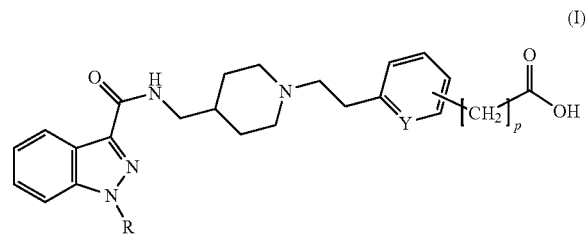

24 Claims, 1 Drawing Sheet

OTHER PUBLICATIONS

Rees, S. et al., "Cloning and Characterisation of the Human 5-HT$_{5A}$Serotonin Receptor", FEBS Letters, vol. 355, pp. 242-246 (1994).

Monsma, F. J. et al., "Cloning and Expression of a Novel Serotonin Receptor With High Affinity for Tricyclic Psyschotropic Drugs", Molecular Pharmacology, vol. 43, pp. 320-327 (1993).

Roth, B. L. et al., "Binding of Typical and Atypical Antipsychotic Agents to 5-Hydroxytryptamine-6 and 5-Hydroxytryptamine-7 Receptors'", The Journal of Pharmacology and Experimental Therapeutics, vol. 268, No. 3, pp. 1403-1410 (1994).

Shearman, L. P., et al., "Relationship Between [ 125 I] RTI-55-Labeled Cocaine Binding Sites and the Serotonin Transporter in rat Placenta", AM. J. Physiol, vol. 275, pp. C1621-C1629 (1998).

Zhou, Z. et al., "Properties of Herg Channels Stably Expressed in HEK 293 Cells Studied At Physiological Temperature", Biophysical Journal, vol. 74, pp. 230-241 (Jan. 1998).

Seltzer, Z. et al., "A Novel Behavioral Model of Neuropathic Pain Disorders Produced in Rats by Partial Sciatic Nerve Injury", Basic Section, Pain, vol. 43 pp. 205-218 (1990).

Bennett, G. J. et al., "A Peripheral Mononeuropathy in Rat That Produces Disorders of Pain Sensation Like Those Seen in Man ", Pain, vol. 33 pp. 87-107 (1988).

FIG. 1

DRUG ACTIVE IN NEUROPATHIC PAIN

CROSS REFERENCES TO RELATED APPLICATIONS

This application is a 371 of International Patent Application No. PCT/EP08/65081, filed on Nov. 6, 2008, and claims priority to European Patent Application No. 07425709.8, filed on Nov. 12, 2007.

FIELD OF THE INVENTION

The present invention relates to a novel indazole, to a process for preparing it and to a pharmaceutical composition comprising it. The invention also relates to the use of an indazole for preparing a pharmaceutical composition that is active in the treatment of neuropathic pain.

PRIOR ART

Chronic pain represents a series of pathologies from which, on average, about 10-20% of the adult population suffers. Chronic pain is generally associated with clinical conditions characterized by chronic and/or degenerative lesions.

Chronic pain differs from acute pain mainly by the duration. Acute pain has a duration of a few days or weeks, correlated with recovery from the event that caused the pain (trauma, burns, intense efforts, surgical or dental interventions, and the like). On the other hand, chronic pain persists for months and even years, causing muscular tension, limited mobility, fatigue, loss of appetite and apathy.

Typical examples of pathologies characterized by chronic pain are rheumatoid arthritis, osteoarthritis, fibromyalgia, neuropathies, etc. [Ashburn MA, Staats PS. Management of chronic pain. Lancet 1999; 353: 1865-69].

Chronic pain, and in particular neuropathic pain, is often debilitating and is a cause of loss of working capacity and of poor quality of life. Economic and social damage thus also follow.

The analgesic drugs currently used in the treatment of neuropathic pain include non-steroidal anti-inflammatory drugs (NSAID), anti-depressants, opioid analgesics, and anti-convulsants [Woolf C J, Mannion R J, Neuropathic pain: aetiology, symptoms, mechanism, and management. Lancet 1999; 353: 1959-1964].

However, chronic pain, and in particular neuropathic pain, is notoriously difficult to treat with the drugs currently available. Consequently, the development of novel drugs has always been one of the main objectives of the pharmaceutical industry.

In addition, despite the numerous research efforts directed towards identifying a suitable analgesic compound, there is a significant number of patients whose pain condition still lacks a suitable treatment [Scholz J, Woolf C J. Can we conquer pain? Nat. Neusci. 2002; 5: 1062-76].

Certain drugs active on the serotoninergic system were considered capable of controlling chronic pain and in particular neuropathic pain.

Patent applications EP-A-0 975 623 and WO 98/46589 relate to numerous compounds of formula 1:

(1)

included those where R6 is represented by an aryl, possibly substituted with a hydroxyl or halogen group. According to the above-mentioned documents, the compounds of formula (A) have affinity towards the $5HT_4$ receptors and act as partial agonist or antagonist of the serotonin, and it has been suggested to use them in the treatment of gastrointestinal motility disorders, urinary incontinence, cardiac arrhythmia and central nervous system disorders such as memory disorders and anxiety.

Patent applications WO 2005/013989 and EP 1 646 387 relate to the use of indazole derivatives for preparing a pharmaceutical composition that is active in the treatment of neuropathic pain, these indazole derivatives being represented by formula 2 below:

(2)

in which X may be N or CH, and, when X is N, R is hydrogen, and when X is CH, R is a hydrogen atom, a hydroxyl group, an alkyl with a linear or branched chain containing from 1 to 3 carbon atoms, an alkoxy with a linear or branched chain containing from 1 to 3 carbon atoms, or a halogen atom.

Patent application WO2004/101548 relates to the use of certain indazole derivatives for preparing a pharmaceutical composition that is active in the treatment of chronic pain. Some of the indazole derivatives disclosed in WO2004/101548 are represented by formula 3 below:

(3)

where $R_a$ is H, $NH_2C(O)$, $CH_3C(O)NH$, $CH_3SO_2$, $CH_3SO_2NH$, linear or branched $C_1$-$C_3$ alkyl, linear or branched $C_1$-$C_3$ alkoxy, or halogen; $R_b$ is H, linear or branched $C_1$-$C_6$ alkyl; aryl-($C_1$-$C_3$)alkyl optionally substituted with 1 or 2 halogen atoms, with a $C_1$-$C_3$ alkyl group or a $C_1$-$C_3$ alkoxy group; $R_c$ is hydroxy, amino, di-($C_1$-$C_3$)alkyl-amino, tri-($C_1$-$C_3$)alkyl-ammoniomethyl, nitro, trifluoromethyl, nitrile, $CH_3C(O)NH$, $CH_3SO_2NH$, $CH_3SO_2$, R'R"$NSO_2$, where R' and R" are H, or a linear or branched $C_1$-$C_6$ alkyl, $R_d$ is H, hydroxy, amino, di-($C_1$-$C_3$)alkyl-amino, tri-($C_1$-$C_3$)alkyl-ammoniomethyl, nitro, trifluoromethyl, nitrile, $CH_3C(O)NH$, $CH_3SO_2NH$, $CH_3SO_2$, R'R"$NSO_2$, where R' and R" have the meanings stated above, with the proviso that when $R_a$ and $R_d$ are both H, and $R_b$ is isopropyl, then $R_c$ is not hydroxy.

Unfortunately, the drugs active on the serotoninergic system that are currently used have side and adverse effects which are due to the low selectivity towards other serotoninergic receptors, which often oblige stoppage of the treatment or avoidance of treatment in the case of particular types of patients who, besides the presence of chronic pain, present concomitant pathological conditions on specific systems, such as the cardiovascular system.

In point of fact, interaction with the serotoninergic system, and even more particularly with specific subreceptors such as $5HT_{1B}$ or $5HT_{2A}$, may give rise to adverse effects on the cardiovascular system, inducing effects on the heart rhythm.

In addition, interactions with the hERG ion channel have been observed, which may be responsible for adverse side effects in the cardiovascular system.

DESCRIPTION OF THE INVENTION

It has now been found, surprisingly, that when the group R of formula 2 is represented by a carboxylic or alkenylcarboxylic group, the compounds of formula (B) maintain their action in neuropathic pain, with increased affinity towards the $5HT_4$ serotoninergic receptor and increased selectivity with respect to the other serotoninergic receptors and towards the hERG channel.

Thus, the present invention relates to a compound of formula (I):

(I)

in which:

R is a linear or branched alkyl group containing between 1 and 3 carbon atoms, Y is CH or N, and p is an integer between 0 and 3 and preferably 0 and 1, and salts thereof, either acid-addition salts with a pharmaceutically acceptable organic or mineral acid, or base-addition salts with a pharmaceutically acceptable organic or mineral base.

In a second aspect, the present invention relates to a pharmaceutical formulation comprising an effective amount of a compound of formula (I):

(I)

in which:

R is a linear or branched alkyl group containing between 1 and 3 carbon atoms,

Y is CH or N, and p is an integer between 0 and 3, preferably 0 and 1, and salts thereof, either acid-addition salts with a pharmaceutically acceptable organic or mineral acid, or base-addition salts with a pharmaceutically acceptable organic or mineral base, and at least one pharmaceutically acceptable excipient.

In a third aspect, the present invention relates to a process for preparing a compound of formula (I):

(I)

in which

R is a linear or branched alkyl group containing between 1 and 3 carbon atoms,

Y is CH or N, and p is an integer between 0 and 3, preferably 0 and 1, and salts thereof, either acid-addition salts with a pharmaceutically acceptable organic or mineral acid, or base-addition salts with a pharmaceutically acceptable organic or mineral base, characterized in that it comprises (1) the reaction between the compound of formula A:

(A)

in which:

R has the meaning described above, and A represents an anionic residue of a mineral or organic acid, and the compound of formula B:

in which Y and p have the meaning described above, $R_1$ represents a linear or branched alkyl, aryl, arylalkyl or alkylaryl group containing between 1 and 10 carbon atoms, and X represents a halogen atom, and (2) the subsequent hydrolysis of the ester obtained from reaction (1).

In a fourth aspect, the present invention relates to the use of a compound of formula (I):

in which:
R is a linear or branched alkyl group containing between 1 and 3 carbon atoms,
Y is CH or N, and
p is an integer between 0 and 3, preferably 0 and 1,
and salts thereof, either acid-addition salts with a pharmaceutically acceptable organic or mineral acid, or base-addition salts with a pharmaceutically acceptable organic or mineral base, for the preparation of a pharmaceutical composition that is active in the treatment of neuropathic pain.

Typical examples of compounds represented by the above-mentioned formula (I) are illustrated in the following Table 1. The "Position" column indicates the position of the carboxylic or alkenylcarboxylic group on the aryl relative to the carbon bonded to the N-ethylpiperidino group.

TABLE 1

| Compound | R | X | p | Position |
|---|---|---|---|---|
| 1 | Isopropyl | CH | 0 | Para |
| 2 | Isopropyl | CH | 1 | Para |
| 3 | Isopropyl | CH | 2 | Para |
| 4 | Isopropyl | CH | 3 | Para |
| 5 | Ethyl | CH | 0 | Para |
| 6 | Methyl | CH | 0 | Para |
| 7 | Isopropyl | N | 0 | Para |
| 8 | Isopropyl | N | 1 | Para |
| 9 | Isopropyl | N | 3 | Para |
| 10 | Ethyl | N | 0 | Para |
| 11 | Methyl | N | 0 | Para |
| 12 | Ethyl | N | 1 | Para |
| 13 | Isopropyl | CH | 0 | Meta |
| 14 | Isopropyl | CH | 0 | Ortho |

Typical examples of pharmaceutically acceptable organic and mineral acids are: oxalic acid, maleic acid, methanesulfonic acid, para-toluenesulfonic acid, succinic acid, citric acid, tartaric acid, lactic acid, hydrochloric acid, phosphoric acid, sulfuric acid. Amino acids such as aspartic acid and glutamic acid may also be used as organic acids.

Typical examples of pharmaceutically acceptable organic and mineral bases are: mono-, di- and trialkylamines, for instance methylamine, dimethylamine, trimethylamine, ethylamine, diethylamine, triethylamine, propylamine, dipropylamine, tripropylamine, ethylenediamine, mono-, di- and tri-alkanolamines, for instance monoethanolamine, diethanolamine and triethanolamine; guanidine, morpholine, piperidine, pyrrolidine, piperazine, 1-butylpiperidine, 1-ethyl-2-methylpiperidine, N-methylpiperazine, 1,4-dimethylpiperazine, N-benzylphenylethylamine, N-methylglucosamine, tris(hydroxymethyl)aminomethane, ammonia, sodium hydroxide, calcium hydroxide, potassium hydroxide, aluminium hydroxide, iron hydroxide, magnesium hydroxide and zinc hydroxide. Amino acids such as arginine and lysine may also be used as organic bases.

Typical examples of pathologies characterized by neuropathic pain are diabetes, cancer, immunodeficiency, trauma, ischemia, multiple sclerosis, sciatica, trigeminal neuralgia and post-herpetic syndrome.

Preferably, the pharmaceutical compositions of the present invention are prepared in the form of suitable dosage forms including an effective dose of at least one compound (I) or a salt thereof, either an acid-addition salt with a pharmaceutically acceptable organic or mineral acid, or a base-addition salt with pharmaceutically acceptable organic and mineral bases, and at least one pharmaceutically acceptable excipient.

The term "pharmaceutically acceptable excipient" is intended to mean, without any particular limitations, a material that is suitable for preparing a pharmaceutical composition to be administered to a living being.

These materials, known in the art, are, for example, release agents, binders, disintegrants, fillers, diluents, dyes, fluidizers, glidants, lubricants, preserving agents, stabilizers, humectants, absorbents, surfactants, buffers, salts for regulating the osmotic pressure, emulsifiers, flavourings and sweeteners.

Useful examples of pharmaceutically acceptable excipients are sugars, such as lactose, glucose or sucrose, starches, such as corn starch and potato starch, cellulose and derivatives thereof, such as sodium carboxymethylcellulose, ethylcellulose and cellulose acetate, gum tragacanth, malt, gelatin, talc, cocoa butter, waxes, oils, such as groundnut oil, cottonseed oil, safflower oil, sesame oil, olive oil, corn oil and soybean oil, glycols, such as propylene glycol, polyols, such as glycerol, sorbitol, mannitol and polyethylene glycol, esters, such as ethyl oleate and ethyl laurate, agar, buffers, such as magnesium hydroxide and aluminium hydroxide, alginic acid, water, isotonic solutions, ethanol, buffer solutions, polyesters, polycarbonates, polyanhydrides, and the like.

Examples of suitable dosage forms are tablets, capsules, coated tablets, granules, solutions and syrups for oral administration; antiseptic plasters, solutions, pastes, creams and ointments for transdermal administration; suppositories for rectal administration and sterile solutions for injection or aerosol administration.

Other suitable dosage forms are sustained-release forms or liposome-based forms, for either the oral or injection route.

When required for particular therapies, the pharmaceutical composition of the present invention may contain other pharmacologically active ingredients whose simultaneous administration is useful.

The amount of compound (I) or acid-addition salt or base-addition salt thereof in the pharmaceutical composition of the present invention may vary within a wide range as a function of known factors, for instance the type of pathology with which the neuropathic pain to be treated is associated, the severity of the affliction, the weight of the patient, the dosage form, the selected route of administration, the number of daily administrations and the efficacy of the selected compound of formula (I). However, the optimum amount may be readily and routinely determined by a person skilled in the art.

Typically, the amount of compound (I) or acid-addition salt or base-addition salt thereof in the pharmaceutical composition of the present invention will be such that it ensures a level of administration of between 0.001 and 100 mg/kg/day of compound (I), expressed as base. Preferably, the level of administration will be between 0.05 and 50 mg/kg/day and even more preferably between 0.1 and 10 mg/kg/day.

The dosage forms of the pharmaceutical composition of the present invention may be prepared according to techniques well known to pharmaceutical chemists, including mixing, granulation, compression, dissolution, sterilization and the like.

In the production process of the present invention, the residue A is preferably represented by halide (such as chloride, bromide or iodide), phosphate (such as pyrophosphate, monophosphate, diphosphate or triphosphate), sulfate, nitrate, or an organic carboxylate (such as acetate, benzoate, lactate and the like). The residue A is more preferably represented by halide, in particular chloride.

In the production process of the present invention, the residue X is preferably represented by halide, more preferably by chloride, bromide or iodide. The preferred residue X is bromide.

In the production process of the present invention, the group represented by $R_1$ is preferably a linear or branched alkyl containing 1-6 carbon atoms, an aryl, an arylalkyl or an alkylaryl containing 7-8 carbon atoms. The group $R_1$ may also comprise conventional organic substituents, such as halide, nitro, hydroxy, and the like. The group $R_1$ is preferably selected from methyl, ethyl, isopropyl, phenyl and benzyl.

Reaction (1) of the production process of the present invention is preferably performed in an organic solvent. Typical examples of organic solvents that are useful in the production process of the present invention are preferably polar aprotic solvents, such as ketones (for example acetone or methyl ethyl ketone), tetrahydrofuran, dimethylformamide, dimethyl sulfoxide, dioxane, acetonitrile and the like.

Reaction (1) of the production process of the present invention is performed under hot conditions, preferably at the boiling point of the reaction solution.

Reaction (1) of the production process of the present invention is preferably performed in the presence of a basic organic or mineral compound. Useful examples of basic organic substances are aliphatic or aromatic amines, such as mono-, di- or trialkylamines, mono-, di- or trialkanolamines, benzylamine, N-methylbenzylamine and the like. Useful examples of mineral bases are strong bases such as NaOH or KOH, or weak bases such as $NH_4OH$, $Na_2CO_3$ and the like.

Reaction (1) of the production process of the present invention is preferably performed in the presence of an activating agent, for instance potassium iodide, caesium iodide, tetrabutylammonium iodide or trimethylphenylammonium iodide.

The hydrolysis (2) of the ester obtained from reaction (1) of the production process of the present invention is performed by methods known in the art. Preferably, the hydrolysis is performed in polar protic organic solvents, for instance methanol, ethanol, propanol, isopropanol, butanol and the like or aprotic organic solvents such as methyl ethyl ketone, tetrahydrofuran, dimethylformamide, dimethyl sulfoxide, dioxane, acetonitrile and the like, and in the presence of a base such as NaOH or KOH.

The preparation of the compounds of formula (A) may be performed according to the process described in patent EP 0 975 623 B1.

The preparation of the compounds of formula (B) may be performed as described in the Journal of the American Chemical Society (1940), 62 1435-8.

The analgesic activity of compound (I) was demonstrated by means of an experimental model in rats represented by the allodynia induced by ligature of the sciatic nerve.

As is known to those skilled in the art, the above-mentioned experimental model may be considered as predictive of activity in man.

The experimental model of ligature of the sciatic nerve in rats represents a neuropathy that reproduces a series of responses similar to those observed in man in numerous traumatic and pathological conditions associated with neuropathic pain. The reason for this is that ligature of the sciatic nerve is capable of inducing a syndrome associated with the activation of specific circuits dedicated to controlling the perception of pain and characterized by the appearance of allodynia, hyperalgia and spontaneous pain. This model is well known to constitute a valid instrument for studying drugs to be used in the treatment of neuropathic pain in man, and in particular in controlling conditions such as allodynia and hyperalgia.

Typical examples of human pathologies characterized by the dysfunctions described in the abovementioned experimental model and characterized by the presence of neuropathic pain are diabetes, cancer, immunodeficiency, trauma, ischemia, multiple sclerosis, sciatica, trigeminal neuralgia and post-herpetic syndrome.

Confirmation of the binding to the serotoninergic receptors was performed by means of the biochemical test on purified membranes from recombinant human cells that stably express the specific receptors or from animal tissues selected as described in particular for each type of serotoninergic receptor, in: Martin G. R. and Humphrey P. P. A. *Neuropharmacol.* 1994, 33:261; Hoyer D. *Eur. J. Pharmacol.* 1985, 118:1; Bonhaus DW et al. *Br. J. Pharmacol.* 1995, 115:622; Wolf WA et al. *J. Neurochem.* 1997, 69:1449; Boess F G et al. *Neuropharmacol.* 1997, 36:637; Mialet J et al. *Br. J. Pharmacol.* 2000; 129:771; Rees S et al. *FEBS Lett.* 1994, 355: 242; Monsma F. J. et al. *Mol. Pharmacol.* 1993, 43:320; Roth BL et al. *J. Pharmacol. Exp. Ther.* 1994, 268: 1403; and Shearman L P et al. *Am. J. Physiol.* 1998, 275: C1621.

As is known to those skilled in the art, this test constitutes a predictive model of molecular interaction and of selectivity with the selected receptors.

Confirmation of interaction with the potassium channels was made by means of a functional cell test (patch clamp) that uses HEK-293 recombinant human cells that stably express the hERG ion channel, as described in Zhou Z. et al. *Biophys. J.* 1998; 74:230.

As is known to those skilled in the art, this test constitutes a predictive model of induction of changes in heart functionality and in particular of effects on the heart rhythm following changes in the Qt time.

TESTS

1. Allodynia Induced by Ligature of the Sciatic Nerve in Rats

Male CD rats weighing 200-250 g on arrival were used.

The allodynia was induced by ligature under anaesthesia of the sciatic nerve of the left hindleg [Seltzer Z, Dubner R, Shir Y. A novel behavioral model of neuropathic pain disorders produced in rats by partial sciatic nerve injury. Pain 1990; 43: 205-218; Bennet GJ, Xie YK. A peripheral mononeuropathy in rat that produces disorders of pain sensation like those seen in man. Pain 1988; 33: 87-107]. At least two weeks after ligature of the sciatic nerve, rats who showed a reduction of at least 50% in the response threshold recorded before the intervention were selected. The pain threshold was measured with a von Frey machine, which makes it possible, by applying a gradual increase in pressure to the paw of the left hindleg of the rat, to record the nociceptive response, expressed in grams, corresponding to the moment at which the animal withdraws the leg.

At 30 minutes, 1, 2 and 4 hours of treatment, the pain threshold measured in control animals was compared with that measured in animals treated with the test product (compound 1 of Table 1).

Figure 1:
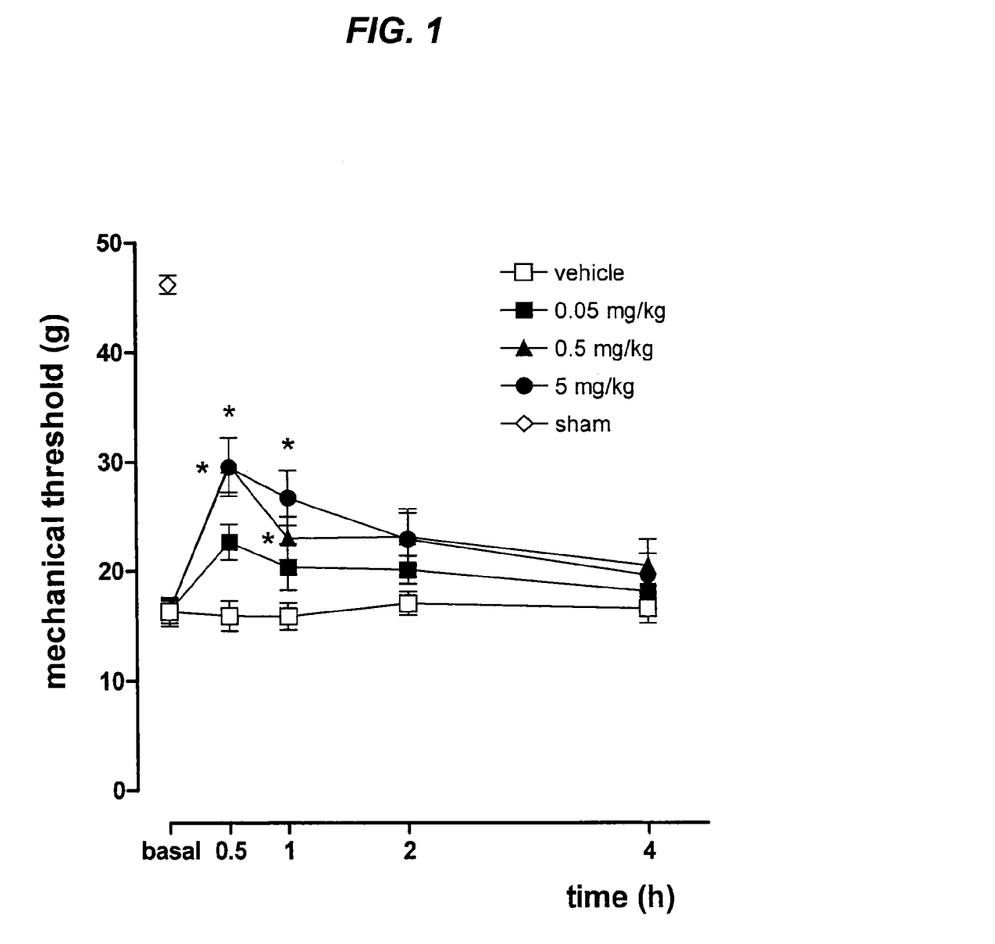
FIG. 1 shows the pain threshold as a function of time for animals treated with the test product (compound 1) as compared to control animals as described in Test 1, below.

The control animals were treated with the same vehicle (methylcellulose) used to administer the test product. The results are illustrated in FIG. 1.

2. Binding to the Serotoninergic Receptors

Confirmation of the binding to the serotoninergic receptors was made using purified membranes from selected animal tissues or from recombinant human cells that stably express the specific receptors, as described in: Martin G. R. and Humphrey P. P. A. *Neuropharmacol.* 1994, 33:261; Hoyer D. *Eur. J. Pharmacol.* 1985, 118:1; Bonhaus DW et al. *Br. J. Pharmacol.* 1995, 115:622; Wolf WA et al. *J. Neurochem.* 1997, 69:1449; Boess FG et al. *Neuropharmacol.* 1997, 36:637; Mialet J et al. *Br. J. Pharmacol.* 2000, 129:771; Rees S et al. *FEBS Lett.* 1994, 355:242; Monsma F. J. et al. *Mol. Pharmacol.* 1993, 43:320; Roth BL et al. *J. Pharmacol. Exp. Ther.* 1994, 268: 1403; and Shearman LP et al. *Am. J. Physiol.* 1998, 275: C1621.

Under the experimental conditions used, compound 1 of Table 1 showed selective inhibition of binding to the 5-HT4 receptor. The results obtained are given in Table 2.

TABLE 2

| Receptor | IC50 (nM) |
|---|---|
| 5-HT$_{1A}$ | >10 000 |
| 5-HT$_{1B}$ | >10 000 |
| 5-HT$_{2A}$ | >10 000 |
| 5-HT$_{2B}$ | >10 000 |
| 5-HT$_{2C}$ | >10 000 |
| 5-HT$_3$ | >10 000 |
| 5-HT$_4$ | 0.8 |
| 5-HT$_{5A}$ | >10 000 |
| 5-HT$_6$ | >10 000 |
| 5-HT$_7$ | >10 000 |
| 5-HT transporter - SERT | >10 000 |

3. Interaction with Potassium Channels (hERG)

Confirmation of interaction with the potassium channels was made by means of the patch clamp test described in Zhou Z. et al. *Biophys. J.* 1998; 74:230 using the recombinant human cell line HEK-293, which stably expresses the hERG ion channel.

Under the experimental conditions used, compound 1 of Table 1 showed an IC50>50 µM. The results obtained are given in Table 3.

TABLE 3

| µM | % inhibition |
|---|---|
| 0.01 | 0.0 |
| 0.10 | 0.0 |
| 1.00 | 0.9 |
| 10.00 | 6.5 |
| 50.00 | 18.8 |

EXAMPLES

Example 1

Preparation of Compound 1 of Table 1

4-{2-[4-({[(1-Isopropyl-1H-indazol-3-yl)carbonyl]amino}methyl)piperidin-1-yl]ethyl}benzoic acid

1a) 1-[4-(2-Bromoethyl)phenyl]ethanone

A solution containing acetyl chloride (85 ml; 0.85 mol) and bromoethylbenzene (82 ml; 0.60 mol) was added, at 0° C., to a mixture containing anhydrous aluminium trichloride (72 g; 0.54 mol), dichloromethane (300 ml) and acetyl chloride (42.5 ml; 0.6 mol). The mixture was stirred under cold conditions for 3 hours and then added to a cold solution of 6N HCl (600 ml). The resulting mixture was stirred at room temperature overnight.

The two phases formed after leaving to stand at room temperature for a few minutes were separated. The acidic phase was extracted twice with 300 ml of dichloromethane. The combined organic phases were washed three times with 100 ml of water and once with 100 ml of saturated NaCl solution, and then dried with anhydrous Na$_2$SO$_4$. The solvent was then evaporated off under reduced pressure, to give 138 g of crude product, which product was subsequently purified by fractional distillation under reduced pressure. 79.0 g (0.35 mol) of 1-[4-(2-bromoethyl)phenyl]ethanone were thus obtained (T=120° C.; P=7 mmHg).

$^1$H NMR (δ ppm, CDCl$_3$, 300 MHz): 2.59 (s, 3 H) 3.23 (t, J=7.31 Hz, 2 H) 3.59 (t, J=7.31 Hz, 2 H) 7.31 (d, J=7.89 Hz, 2H) 7.92 (d, J=8.18 Hz, 2 H).

2a) 4-(2-Bromoethyl)benzoic acid

A solution containing 1-[4-(2-bromoethyl)phenyl]ethanone (38.2 g; 0.17 mol) in dioxane (100 ml) was added slowly to a solution containing bromine (80.6 g; 0.50 mol), sodium hydroxide (55.4 g; 1.39 mol), water (470 ml) and dioxane (340 ml) stirred at 0° C. The mixture was stirred at the same temperature for 3 hours, followed by addition, while still cold, of 120 ml of concentrated HCl. The resulting mixture was stirred at room temperature overnight.

The solid obtained from the mixture was filtered off and washed on the filter with 1N HCl (200 ml). 20.3 g of 4-(2-bromoethyl)benzoic acid (0.09 mol) were thus obtained, and were used for the following reaction without further purification.

$^1$H NMR (δ ppm, 300 MHz, DMSO-d6): 3.21 (t, J=6.95 Hz, 2 H) 3.77 (t, J=7.14 Hz, 2 H) 7.40 (d, J=8.42 Hz, 2 H) 7.89 (d, J=8.05 Hz, 2 H) 12.83 (s, 1 H).

3a) Ethyl 4-(2-bromoethyl)benzoate

A mixture containing 4-(2-bromoethyl)benzoic acid (10 g; 43.7 mmol), 9.5 N hydrochloric ethanol (50 ml; 475 mmol) and absolute ethanol (50 ml) was stirred at reflux for 4 hours.

The mixture was then cooled to room temperature and the solvent was evaporated off under reduced pressure. The residue was taken up in saturated Na$_2$CO$_3$ solution (100 ml) and then extracted with ethyl acetate (3×100 ml).

The combined organic phases were washed first with water (50 ml) and then with saturated NaCl solution (30 ml). The solution was then dried with anhydrous Na$_2$SO$_4$. Finally, the solvent was evaporated off under reduced pressure, thus giving 10.8 g of ethyl 4-(2-bromoethyl)benzoate (42 mmol), which was used in the following reaction without further purification.

$^1$H NMR (δ ppm, 300 MHz, CDCl$_3$) 1.39 (t, J=6.87 Hz, 3 H) 3.22 (t, J=7.45 Hz, 2 H) 3.58 (t, J=7.45 Hz, 2 H) 4.37 (q, J=6.90 Hz, 2 H) 7.28 (d, J=8.15 Hz, 2 H) 8.00 (d, J=8.18 Hz, 2 H)

4a) Ethyl 4-{2-[4-({[(1-isopropyl-1H-indazol-3-yl)carbonyl]amino}-methyl)piperidin-1-yl]ethyl}benzoate A mixture containing 1-isopropyl-N-(piperidin-4-ylmethyl)-1H-indazol-3-carboxamide hydrochloride (45.9 g, 136 mmol), prepared as described in EP 0 975 623, ethyl 4-(2-bromoethyl)benzoate (37 g; 144 mmol), 2-butanone (1600 ml) and triethylamine (18.9 ml; 136 mmol) was stirred at reflux. After reaction for 1.5 hours, a second aliquot of triethylamine (9.5 ml; 68 mmol) was added, while maintaining the reflux. After reaction for a further 1.5 hours, a third aliquot of triethylamine (9.5 ml; 68 mmol) was added, while maintaining the reflux. After a further 1.5 hours, potassium iodide (6.2 g; 37.3 mmol) was added to the reaction mixture, while still at reflux. Finally, the mixture was then stirred at reflux overnight.

The resulting mixture was then cooled to room temperature and poured into water (2 L). The two phases were separated and the aqueous phase was extracted with 2-butanone (2×400 ml). The combined organic phases were then washed with water (50 ml) and with saturated NaCl solution (50 ml). The solution was dried with anhydrous Na$_2$SO$_4$ and the solvent was then evaporated off under reduced pressure. 58.9 g of crude product were obtained, which product was purified by gravity chromatography on neutral alumina (1400 g), using an 8/2 mixture of chloroform and hexane as eluent.

14.2 g of ethyl 4-{2-[4-({[(1-isopropyl-1H-indazol-3-yl)carbonyl]-amino}methyl)piperidin-1-yl]ethyl}benzoate (29.8 mmol) were thus obtained.

$^1$H NMR (δ ppm, 300 MHz, CDCl$_3$): 1.32-1.51 (m, 2 H) 1.38 (t, J=7.16 Hz, 3 H) 1.61 (d, J=6.72 Hz, 6 H) 1.64-1.91 (m, 3 H) 2.05 (td, J=11.55, 2.34 Hz, 2 H) 2.54-2.66 (m, 2 H) 2.81-2.91 (m, 2 H) 3.02 (d, J=11.69 Hz, 2 H) 3.42 (t, J=6.43 Hz, 2 H) 4.36 (q, 2 H) 4.87 (spt, 1 H) 7.15 (t, J=6.28 Hz, 1 H) 7.22-7.31 (m, 3 H) 7.35-7.49 (m, 2 H) 7.96 (d, 2 H) 8.39 (dt, J=8.18, 1.02 Hz, 1 H).

5a) 4-{2-[4-({[(1-Isopropyl-1H-indazol-3-yl)carbonyl]amino}methyl)piperidin-1-yl]ethyl}benzoic acid The solution containing ethyl 4-{2-[4-({[(1-isopropyl-1H-indazol-3-yl)carbonyl]amino}methyl)piperidin-1-yl]ethyl}benzoate (6.2 g; 13 mmol), tetrahydrofuran (30 ml), absolute ethanol (30 ml) and 1N sodium hydroxide (28.5 ml; 28.5 mmol) was stirred at room temperature for 3 days. The resulting mixture was neutralized to pH 7 by adding glacial acetic acid (about 1.7 ml) and was then stirred at room temperature overnight.

The solid thus formed was filtered off while cold and was then washed on the filter with a 1/1 mixture of tetrahydrofuran and absolute ethanol. The solid was crystallized several times from a 4/3 mixture of ethyl acetate and ethanol. 3.7 g of 4-{2-[4-({[(1-Isopropyl-1H-indazol-3-yl)carbonyl]amino}methyl)piperidin-1-yl]ethyl}benzoic acid (8.3 mmol) were thus obtained.

$^1$H NMR (δ ppm, 300 MHz, DMSO-d6) 1.23 (d, J=11.34 Hz, 2 H) 1.53 (d, J=6.59 Hz, 6 H) 1.57-1.77 (m, 3 H) 2.01 (t, J=10.79 Hz, 2 H) 2.57 (t, J=8.00 Hz, 2 H) 2.81 (t, J=7.68 Hz, 2 H) 2.96 (d, J=10.98 Hz, 2 H) 3.21 (t, J=6.22 Hz, 2 H) 5.06 (spt, J=6.62 Hz, 1 H) 7.21-7.28 (m, 1 H) 7.31 (d, J=8.05 Hz, 2 H) 7.42 (ddd, J=8.51, 7.04, 1.28 Hz, 1 H) 7.76 (d, J=8.42 Hz, 1 H) 7.84 (d, J=8.05 Hz, 2 H) 8.12-8.24 (m, 2 H) 10.78 (br. s., 1 H).

m.p.=179-181° C.; MS showed 449 (MH$^+$) base peak;

Elemental analysis for C$_{26}$H$_{32}$N$_4$O$_3$

|  | C | H | N |
|---|---|---|---|
| % found | 69.37 | 7.23 | 12.25 |
| % calculated | 69.62 | 7.19 | 12.49 |

Example 2

A tablet containing, as active principle, Compound 1 of the present invention, has the following composition:

| | |
|---|---|
| Active principle | 50 mg |
| Lactose monohydrate | 161 mg |
| Dibasic calcium phosphate dehydrate | 161 mg |
| Microcrystalline cellulose | 95 mg |
| Corn starch | 30 mg |
| Sodium carboxymethylstarch | 24 mg |
| Povidone | 11 mg |
| Magnesium stearate | 3 mg |

Example 3

A vial containing, as active principle, Compound 1 of the present invention, has the following composition:

| | |
|---|---|
| Active principle | 25 mg |
| Sorbitol | qs iso-osmotic solution |
| Water | qs 100 ml |

Example 4

A pharmaceutical composition in the form of granules containing, as active principle, Compound 1 of the present invention, has the following composition:

| | |
|---|---|
| Active principle | 50 mg |
| Maltitol | 1300 mg |
| Mannitol | 2700 mg |
| Sucrose | 1000 mg |
| Citric acid | 20 mg |
| Aspartame | 20 mg |
| Flavourings | 200 mg |

The invention claimed is:

1. A process for preparing a compound of formula (I):

wherein:
R is a linear or branched alkyl group containing 1 to 3 carbon atoms,
Y is CH or N, and
p is an integer of 0 to 3,
or a salt thereof,
wherein said process comprises:
(1) reacting a compound of formula A:

in which A represents an anionic residue of a mineral or organic acid,
with a compound of formula B:

in which $R_1$ represents a linear or branched alkyl group, an aryl group, an arylalkyl group, or an alkylaryl group containing 1 to 10 carbon atoms, and X represents a halogen atom, to obtain an ester of the compound of formula (I); and
(2) hydrolyzing said ester of the compound of formula (I) to produce said compound of formula (I) or a salt thereof.

2. A process according to claim 1, wherein said residue A is selected from the group consisting of halide, phosphate, sulfate, nitrate, and organic carboxylate.

3. A process according to claim 2, wherein said residue A is selected from the group consisting of chloride, bromide, and iodide.

4. A process according to claim 1, wherein said residue X is selected from the group consisting of chloride, bromide, and iodide.

5. A process according to claim 1, wherein $R_1$ is selected from the group consisting of a linear alkyl group containing 1-6 carbon atoms, a branched alkyl group containing 1-6 carbon atoms, an aryl group, an arylalkyl group, and an alkylaryl group containing 7-8 carbon atoms.

6. A process according to claim 1, wherein said reacting (1) is performed in an organic solvent which is a polar aprotic solvent.

7. A process according to claim 6, wherein said organic solvent is selected from the group consisting of acetone, methyl ethyl ketone, tetrahydrofuran, dimethylformamide, dimethyl sulfoxide, dioxane, and acetonitrile.

8. A process according to claim 1, wherein said reacting (1) is performed in the presence of a basic organic or mineral compound.

9. A process according to claim 1, wherein said reacting (1) is performed in the presence of an activating agent selected from the group consisting of potassium iodide, caesium iodide, tetrabutylammonium iodide, and trimethylphenylammonium iodide.

10. A process according to claim 2, wherein said reacting (1) is performed in an organic solvent which is a polar aprotic solvent.

11. A process according to claim 10, wherein said organic solvent is selected from the group consisting of acetone, methyl ethyl ketone, tetrahydrofuran, dimethylformamide, dimethyl sulfoxide, dioxane, and acetonitrile.

12. A process according to claim 3, wherein said reacting (1) is performed in an organic solvent which is a polar aprotic solvent.

13. A process according to claim 12, wherein said organic solvent is selected from the group consisting of acetone, methyl ethyl ketone, tetrahydrofuran, dimethylformamide, dimethyl sulfoxide, dioxane, and acetonitrile.

14. A process according to claim 4, wherein said reacting (1) is performed in an organic solvent which is a polar aprotic solvent.

15. A process according to claim 14, wherein said organic solvent is selected from the group consisting of acetone, methyl ethyl ketone, tetrahydrofuran, dimethylformamide, dimethyl sulfoxide, dioxane, and acetonitrile.

16. A process according to claim 5, wherein said reacting (1) is performed in an organic solvent which is a polar aprotic solvent.

17. A process according to claim 16, wherein said organic solvent is selected from the group consisting of acetone, methyl ethyl ketone, tetrahydrofuran, dimethylformamide, dimethyl sulfoxide, dioxane, and acetonitrile.

18. A process according to claim 2, wherein said reacting (1) is performed in the presence of an activating agent selected from the group consisting of potassium iodide, caesium iodide, tetrabutylammonium iodide, and trimethylphenylammonium iodide.

19. A process according to claim 3, wherein said reacting (1) is performed in the presence of an activating agent selected from the group consisting of potassium iodide, caesium iodide, tetrabutylammonium iodide, and trimethylphenylammonium iodide.

20. A process according to claim 4, wherein said reacting (1) is performed in the presence of an activating agent selected from the group consisting of potassium iodide, caesium iodide, tetrabutylammonium iodide, and trimethylphenylammonium iodide.

21. A process according to claim 5, wherein said reacting (1) is performed in the presence of an activating agent selected from the group consisting of potassium iodide, caesium iodide, tetrabutylammonium iodide, and trimethylphenylammonium iodide.

22. A process according to claim 6, wherein said reacting (1) is performed in the presence of an activating agent selected from the group consisting of potassium iodide, caesium iodide, tetrabutylammonium iodide, and trimethylphenylammonium iodide.

23. A process according to claim 7, wherein said reacting (1) is performed in the presence of an activating agent selected from the group consisting of potassium iodide, caesium iodide, tetrabutylammonium iodide, and trimethylphenylammonium iodide.

24. A process according to claim 8, wherein said reacting (1) is performed in the presence of an activating agent selected from the group consisting of potassium iodide, caesium iodide, tetrabutylammonium iodide, and trimethylphenylammonium iodide.

* * * * *